United States Patent [19]

Motegi et al.

[11] 4,170,585

[45] Oct. 9, 1979

[54] ADHESIVE COMPOSITION

[75] Inventors: Akira Motegi; Kaoru Kimura, both of Nagoya, Japan

[73] Assignee: Toagosei Chemical Industry Co., Ltd., Tokyo, Japan

[21] Appl. No.: 931,584

[22] Filed: Aug. 7, 1978

[30] Foreign Application Priority Data

Aug. 5, 1977 [JP] Japan ............................... 52/93407

[51] Int. Cl.$^2$ .............................................. C08K 5/06
[52] U.S. Cl. ..................... 260/33.2 R; 260/31.4 R; 260/32.6 N; 428/428; 428/451; 428/463; 428/494; 428/514; 428/518; 526/245; 526/285; 526/298; 526/312
[58] Field of Search ............................. 526/312, 298; 260/33.2 R, 32.6 N, 31.4 R

[56] References Cited

U.S. PATENT DOCUMENTS

| | | | |
|---|---|---|---|
| 3,260,637 | 7/1966 | von Bramer | 260/30.6 R |
| 3,699,127 | 10/1972 | O'Sullivan et al. | 260/33.2 |

*Primary Examiner*—Stanford M. Levin
*Attorney, Agent, or Firm*—Sughrue, Rothwell, Mion, Zinn and Macpeak

[57] ABSTRACT

An adhesive composition comprising an α-cyanoacrylate and about 0.0001% by weight to about 20% by weight, based on the weight of the adhesive composition, of at least one compound selected from the group consisting of (1) polyethylene glycols having a degree of polymerization of at least 3, and (2) non-ionic surface active agents having a poly(ethyleneoxy) moiety therein with the poly(ethyleneoxy) moiety having a degree of polymerization of at least 3.

10 Claims, No Drawings

ADHESIVE COMPOSITION

BACKGROUND OF THE INVENTION

1. Field of the Invention

This invention relates to an α-cyanoacrylate-type adhesive composition, and more specifically to an α-cyanoacrylate-type adhesive composition which has good storage stability and is rapidly curable with a fast setting time.

2. Description of the Prior Art

An α-cyanoacrylate monomer, a principal component of an α-cyanoacrylate-type adhesive composition, has unique anionic polymerizability, and begins to polymerize in the presence of a weak anion such as the slight amount of moisture adhering to the surface of an adherend. Consequently, an α-cyanoacrylate-type adhesive composition can be used to bond almost all materials, except for some inert materials such as polyethylene and Teflon (trademark for polytetrafluoroethylene resins produced by E. I. du Pont de Nemours), firmly within several seconds to several minutes. An α-cyanoacrylate-type adhesive has therefore gained widespread acceptance as an instantaneous adhesive in industrial, medical and household applications.

The curing of an α-cyanoacrylate-type adhesive is based on the anionic polymerization of the α-cyanoacrylate monomer. The anionic polymerization, however, is inhibited when bonding a adherend having an acidic surface, such as a wooden material, a chemically treated surface (e.g., a chromate-treated surface), or a surface which has the tendency to permit the formation of an acidic oxide coating. Frequently, this causes a retardation in the setting time, and the adhesion strength obtained is not necessarily sufficient. For example, wooden materials generally used have a moisture content of about 10% by weight at a temperature of about 23° C. and a relative humidity of about 55%. When a wooden material is bonded with a conventional α-cyanoacrylate-type adhesive composition, a setting time of several minutes to more than ten minutes is required despite the presence of such a large amount of water in the woody tissue and the surface of the material. It has been generally considered to be difficult to bond wooden materials with α-cyanoacrylate-type adhesive compositions. The reason is believed to be due to the following. The surface of a wooden material is acidic with a pH of about 4 to 6 because of the sap present, and, therefore, in bonding, the anionic polymerization of the α-cyanoacrylate monomer is inhibited and the rate of curing is slow. Furthermore, during this time, the adhesive composition penetrates into the porous woody tissue, and adhesive-free portions in the adhesive layer result.

Various investigations have been made to provide a method for shortening the setting time of α-cyanoacrylate-type adhesive compositions. The most common method is to use a curing agent for promoting the anionic polymerization of the α-cyanoacrylate monomer as a primer or a post-treating agent (for example, as disclosed in U.S. Pat. No. 3,260,637). When both the α-cyanoacrylate monomer and the curing agent are prepared as a one-package adhesive composition, the monomer polymerizes during storage. Hence, they must be stored, and the curing agent described above must be used as a primer on the job. Thus, two coating operations are required to apply both the primer and the adhesive, and the coating efficiency decreases drastically.

SUMMARY OF THE INVENTION

In view of this state of art, extensive investigations have now been made on a method which can accelerate the setting of an α-cyanoacrylate-type adhesive composition without adversely affecting the stability and other properties of the composition, and which can be employed simply and accurately.

The word led to the discovery that the object described above can be achieved by incorporating at least one compound selected from the group consisting of polyethylene glycols and nonionic surface active agents having a poly(ethyleneoxy) moiety into an α-cyanoacrylate-type adhesive composition.

Accordingly, this invention provides an adhesive composition comprising an α-cyanoacrylate and about 0.0001% by weight to about 20% by weight, based on the weight of the adhesive composition, of at least one compound selected from the group consisting of (1) polyethylene glycols having a degree of polymerization of at least 3, and (2) non-ionic surface active agents having a poly(ethyleneoxy) moiety therein, with the poly(ethyleneoxy) moiety having a degree of polymerization of at least 3.

DETAILED DESCRIPTION OF THE INVENTION

The α-cyanoacrylate-type adhesive composition of this invention as described above contains an α-cyanoacrylate monomer of the formula (I)

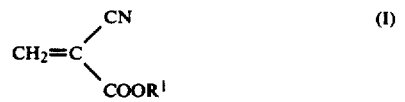

wherein $R^1$ represents a straight chain or branched chain alkyl group having 1 to 12 carbon atoms (which may be substituted with a substituent such as a halogen atom or an alkoxy group) a straight chain or branched chain alkenyl group having 2 to 12 carbon atoms, a straight chain or branched chain alkynyl group having 2 to 12 carbon atoms, a cycloalkyl group, an aralkyl group or an aryl group. Specific examples of the groups for $R^1$ are a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzyl group, a phenyl group, a cresyl group, a 2-chloroethyl group, a 3-chloropropyl group, a 2-chlorobutyl group, a trifluoroethyl group, a 2-methoxyethyl group, a 3-methoxybutyl group and a 2-ethoxyethyl group.

A single α-cyanoacrylate monomer or a mixture of two or more of these α-cyanoacrylate monomers can be used. Generally, the above α-cyanoacrylate monomer alone is not sufficient as an adhesive, and the components set forth below are sometimes added.

(1) An anionic polymerization inhibitor
(2) A radical polymerization inhibitor
(3) A thickener
(4) Special additives such as plasticizers and heat stabilizers
(5) Perfumes, dyes, pigments, etc.

A suitable amount of the α-cyanoacrylate monomer present in the adhesive composition is about 80 to 99.9% by weight preferably 90 to 99.9% by weight, based on the total weight of the adhesive composition.

An anionic polymerization inhibitor is added to the α-cyanoacrylate-type adhesive composition, e.g., in an amount of about 1 to 1000 ppm based on the total weight of the adhesive composition, to increase the stability of the adhesive composition during storage, and examples of known inhibitors are sulfur dioxide, aromatic sulfonic acids, aliphatic sulfonic acids, sultones, and carbon dioxide.

Suitable examples of radical polymerization inhibitors include, for example, hydroquinone and hydroquinone monomethyl ether. A radical polymerization inhibitor is added, e.g., in amount of about 1 to 5000 ppm based on the total weight of the adhesive composition, for the purpose of capturing radicals which are formed by light during storage.

A thickener is added to increase the viscosity of the α-cyanoacrylate-type adhesive composition. The α-cyanoacrylate monomer generally has a low viscosity of about several centipoises, and therefore, the adhesive penetrates into porous materials such as wood and leather or adherends having a rough surface. Thus, good adhesion strengths are difficult to obtain. Various polymers can be used as thickeners, and examples include poly(methyl methacrylate), methacrylate-type copolymers, acrylic rubbers, cellulose derivatives, polyvinyl acetate and poly(α-cyanoacrylate). A suitable amount of thickener is generally about 20% by weight or less based on the total weight of the adhesive composition.

The plasticizers, perfumes, dyes, pigments, etc., may be added depending on use purposes in amounts which do not adversely affect the stability of the α-cyanoacrylte monomer. A suitable amount of the plasticizer is about 0.1 to 50% by weight, of the heat stabilizer is about 0.01 to about 5% by weight and of each of the perfume, the dye and the pigment is about 0.01 to 5% by weight, based on the total weight of the adhesive composition.

The accelerating compound also present in the α-cyanoacrylate adhesive composition of this invention to accelerate the setting of the adhesive composition, i.e., shorten the setting time of the adhesive composition, is at least one compound selected from the group consisting of (1) Polyethylene glycols having a degree of polymerization of at least 3, and (2) non-ionic surface active agents having a poly(ethyleneoxy) moiety therein with the poly(ethyleneoxy) moiety having a degree of polymerization of at least 3.

Suitable polyethylene glycols which can be used are those having a structure of the formula (II)

$$HO{-}(CH_2CH_2O)_n{-}H \quad (II)$$

wherein n is the degree of polymerization and n is at least 3. Usually, they are produced by polymerizing ethylene oxide. Polythylene glycols are commercially available in various molecular weights depending on the degree of polymerization (n). Suitable examples of polyethylene glycols are polyethylene glycol #200 with an average degree of polymerization of 4, polyethylene glycol #300 with an average degree of polymerization of 6, and polyethylene glycols #400, #600, #1000, #1250, #1540, #2000, #3600, #4000, #6000, #20000 with various other degrees of polymerization.

The polyethylene glycol used in this invention should have a degree of polymerization of at least 3, i.e., a molecular weight of at least 150. If the polyethylene glycol has a degree of polymerization of less than 3, the effect of the polyethylene glycol in accelerating the setting of the adhesive composition is extremely small, and the adhesive composition of the present invention can not be obtained. There is no particular upper limit on the degree of polymerization of the polyethylene glycol. Preferably, the degree of polymerization of the polyethylene glycol is about 10,000 or less, more preferably about 3,000 or less. Polyethylene glycols having a degree of polymerization greatly exceeding 10,000 tend to have reduced compatibility with the α-cyanoacrylate monomer, and it is difficult to use such polyethylene glycols since they do not dissolve uniformly in the adhesive composition.

Suitable nonionic surface active agents having a poly(ethyleneoxy) moiety in the molecule thereof which can be used in the present invention can be selected, for example, from the following compounds which are generally known.

(1) Polyethylene glycol alkyl ether-type nonionic surface active agents (2) Polyethylene glycol alkyl phenyl ether-type nonionic surface active agents (3) Polyethylene glycol fatty acid ester-type nonionic surface active agents (4) Polyethylene glycol-polypropylene glycol ether-type nonionic surface active agents (5) Polyethylene glycol sorbitan fatty acid ester-type nonionic surface active agents (6) Ethylene oxide adducts of other active hydrogen-containing compounds (7) Polyethylene glycol alkylamine type nonionic surface active agents Suitable nonionic surface active agents which are effective in this invention are those having a poly(ethyleneoxy) moiety, —CH$_2$CH$_2$-O)$_n$, in the molecule thereof. Furthermore, for the same reason as set forth above for the polyethylene glycol, the degree of polymerization of the poly(ethyleneoxy) moiety should be at least 3. A suitable degree of polymerization (n) for the poly(ethyleneoxy) moiety is about 3 to 200, preferably 3 to 100.

Specific examples of nonionic surface active agents having a poly(ethyleneoxy) moiety which can be used in this invention are listed below. However, these examples are given merely for the purposes of illustration and the present invention is not to be construed as being limited to these examples.

(1) Polyethylene glycol alkyl ether-type nonionic surface active agents:
Polyethylene glycol lauryl ether,
polyethylene glycol cetyl ether,
polyethylene glycol stearyl ether,
polyethylene glycol oleyl ether, etc.

(2) Polyethylene glycol alkyl phenyl ether-type surface active agents:
Polyethylene glycol octyl phenyl ether,
polyethylene glycol nonyl phenyl ether,
polyethylene glycol dodecyl phenyl ether, etc.

(3) Polyethylene glycol fatty acid ester-type nonionic surface active agents:
Polyethylene glycol monolaurate,
polyethylene glycol monostearate, polyethylene glycol monooleate,
polyethylene glycol distearate,
polyethylene glycol stearate (mixture of mono- and di-esters),
polyethylene glycol perfluorolaurate, etc.

(4) Polyethylene glycol-polypropylene glycol ether-type nonionic surface active agents:

Polyethylene glycol-polypropylene glycol ether, etc.

(5) Polyethylene glycol sorbitan fatty acid ester-type nonionic surface active agents:

Polyethylene glycol sorbitan monolaurate,
polyethylene glycol sorbitan monostearate,
polyethylene glycol sorbitan monooleate,
polyethylene glycol sorbitan monopalmitate,
polyethylene glycol sorbitan tristearate,
polyethylene glycol sorbitan trioleate, etc.

(6) Ethylene oxide adducts of active hydrogen-containing compounds:

Phenolic resin/polyethylene oxide adducts,
polyacrylate/polyethylene oxide adducts,
3,6-dimethyl-4-octyne-3,6-diol/polyethylene oxide adducts,
polyethylene glycol lanolin alcohol ether,
polyethylene glycol lanolin fatty acid ester, etc.

(7) Polyethylene glycol alkylamine type nonionic surface active agents:

Polyethylene glycol alkylamine adducts.

The amount of the above accelerating compound present in the α-cyanoacrylate adhesive composition is not particularly limited as long as the setting of the adhesive composition is accelerated without impairing the storage stability of the adhesive composition. Generally, a suitable amount of the accelerating compound ranges from about 0.001% by weight to about 20% by weight, preferably from 0.01% by weight to 10% by weight. Generally, when the amount of the accelerating compound is small, the effect of accelerating the setting is small, although this varies somewhat depending on the type of the accelerating compound used. When the amount of the accelerating compound exceeds about 20% by weight, there is a tendency for the accelerating compound to dissolve with difficulty, for the viscosity of the adhesive composition to increase, or for the adhesive composition to gel during storage. When the amount of the accelerating compound is within the range of about 0.01 to about 10% by weight, a very fast setting time balanced with good storage stability is achieved.

Suitable adherends which can be bonded using the adhesive composition of this invention include not only the wooden materials and chromate-treated metallic materials as described above but also ordinary metallic materials, ceramics, plastics, and rubbers. The adhesive composition of this invention can also be employed in bonding porous materials such as leather and paper.

The adhesive composition of this invention has an extremely fast setting time, and the storage stability of the adhesive composition scarcely changes. The acidification phenomenon (i.e., the phenomenon that during storage, the setting time gradually becomes slower, and finally the adhesiveness of the adhesive composition is lost although the adhesive composition is not gelled) of the adhesive composition can be markedly retarded.

The following Examples and Comparative Examples are given to illustrate the present invention in more detail. In these examples, all % and ppm values are by weight. The properties indicated were measured using the following methods.

(1) Setting Time Measurement

The setting time was measured in accordance with the testing method for setting time set forth in Standards JAI-4 "Method for Testing α-Cyanoacrylate-Type Adhesive" of the Japan Association of Adhesive Industry. The adherend sample had a size of 5×20 (adhering surface)×35 mm. When the adherend sample was wood, the sample had a size of 12.7×12.7×38 mm, and the setting time of the adhesive composition at the grain surface (adhering area: 1.61 m$^2$) parallel to the grain was measured. The moisture content was measured using a Kett wood moisture meter.

(2) Compression Shear Adhesion Strength

Compression shear adhesion strength was measured in accordance with JIS K-6852 "Method for Testing Compression Shear Adhesion Strength of Adhesives." The adhered sample had a size of 12.7×12.7×38 mm. Grain surfaces were bounded to each other with an adhering area of 1.61 cm$^2$. The compression speed was controlled at 20 mm/min.

(3) Tensile Adhesion Strength

Tensile adhesion strength was measured in accordance with Standards JAI-4 "Method for Testing Tensile Adhesion Strength" as in the case of measuring the setting time. The adhered sample used had a size of 5×20 (adhering surface)×35 mm. The tensile speed was controlled at 20 mm/min.

(4) Storage Stability

Storage stability was measured in accordance with Standards JAI-4 "Method for Testing Storage Stability" as in the case of measuring the setting time. The adhesive composition sample was allowed to stand for 5 days at a constant-temperature of 70°±2° C. Then, the change in viscosity and the setting time were compared with those of a control.

EXAMPLE 1 AND COMPARATIVE EXAMPLE 1

To an α-cyanoacrylate-type adhesive comprising an ethyl α-cyanoacrylate monomer, 40 ppm of sulfur dioxide as an anionic polymerization inhibitor and 200 ppm of hydroquinone as a radical polymerization inhibitor was added 0.5% of polyethylene glycol 600 (reagent grade), and the mixture was mixed to form a solution. The solution was applied to the grain surface (finished with an electric planer) of lauan wood (moisture content: 9.8%) as an adhered, and the setting time in an atmosphere maintained at 23° C. and a relative humidity (RH) of 55% was measured. It was found that complete setting occurred in 30 seconds. After standing for 24 hours, the compression shear adhesion strength of the bond was 120 kg/cm$^2$, and the woody tissue of the lauan wood broke.

As Comparative Example 1, the setting time of an α-cyanoacrylate adhesive composition having the same composition as described above but not containing polyethylene glycol 600 was tested under the same conditions as described above. On standing for more than 10 minutes, no adhesion strength was developed, and the adhesive mostly penetrated into the woody tissue of the adherend. The compression shear adhesion strength after 24 hours was only 35 kg/cm$^2$.

The storage stability of the adhesive compositions of Example 1 and Comparative Example 1 were both tested at 70°±2° C., and viscosities and setting times after standing for 5 days of both adhesive compositions were also measured. No difference from the controls was noted.

EXAMPLES 2 TO 12 AND COMPARATIVE EXAMPLES 2 TO 5

Each of the various compounds shown in Table 1 below was added to, and dissolved in, an α-cyanoacrylate-type adhesive comprising an ethyl α-cyanoacrylate monomer, 50 ppm of sulfur dioxide, 500 ppm of hydroquinone and 3% of polymethyl methacrylate as a thickener. Each of the resulting adhesive compositions was applied to the grain surface of balsa wood (moisture content: 6.5%) as an adherend, and the setting time of each of the adhesive compositions was measured in an atmosphere maintained at 20° C. and RH 55%. The results obtained are also shown in Table 1.

Table 1

| Example/ Comparative Example No. | Accelerating Compound Added | Amount (%) | Setting Time on Balsa Wood (seconds) | Storage Stability (70° C. for 5 days) |
|---|---|---|---|---|
| Example No. | | | | |
| 2 | Polyethylene glycol 400 (n ≈ 9) | 0.5 | 1 | Good |
| 3 | Polyethylene oxide (R-150) (n ≈ 2200) | 0.5 | 1 | Good |
| 4 | Polyethylene glycol stearate (n ≈ 12) | 0.5 | 2 | Good |
| 5 | Polyethylene glycol nonyl phenyl ether (n ≈ 46) | 0.5 | 5 | Good |
| 6 | Polyethylene glycol sorbitan monolaurate (n ≈ unknown) | 0.5 | 15 | Good |
| 7 | Polyethylene glycol lauryl ether (n ≈ 4) | 0.5 | 2 | Good |
| 8 | Polyethylene glycol polypropylene glycol ether (molecular weight about 2,000) | 0.5 | 3 | Good |
| Comparative Example No. | | | | |
| 2 | None | — | 45 | Good |
| 3 | Sorbitan monostearate (Sorgen 50, a product of Daiichi Kogyo Seiyaku K.K.) | 1 | 45 | Good |
| 4 | Polyoxyethylene alkyl ether sodium sulfate (Emerl 20C, a product of Kao-Atlas Co., Ltd.) | 0.5 | — | Gelled at time of mixing | n = the degree of polymerizaytion
≈ = about

The compounds added in the Examples had an effect of shortening the setting time, and the resulting adhesive composition had good storage stability. However, the nonionic surface active agent which did not contain a poly(ethyleneoxy) moiety used in Comparative Example 3 did not show any effect in shortening the setting time. As shown in Comparative Example 4, even when a poly(ethyleneoxy) moiety is present, an anionic surfactant causes the α-cyanoacrylate adhesive to gel during mixing.

The compression shear adhesion strengths of the adhesive compositions of Examples 2 to 8, measured under the same conditions as described in Example 1 L on lauan wood, were 115 to 130 kg/cm$^2$ (the woody tissue broke).

EXAMPLES 9 TO 12 AND COMPARATIVE EXAMPLES 5 TO 8

Each of the polyethylene glycols having various degrees of polymerization as shown in Table 2 below was added in an amount of 0.5% to an α-cyanoacrylate-type adhesive comprising a methyl α-cyanoacrylate monomer, 20 ppm of sulfur dioxide and 200 ppm of hydroquinone. Each of the adhesive compositions was applied to the grain surfaces of lauan wood (water content: 9.5%) and balsa wood (water content: 7.5%) as adherends, and the setting time of each adhesive composition was measured in an atmosphere maintained at 23° C. and RH 55%. The results obtained are shown in Table 2 below. The storage stability of each of the adhesive compositions was tested at 70°±2° C., and the results obtained are also shown in Table 2 below.

Table 2

| Example/ Comparative Example No. | Polyethylene Glycol Type | n | Soluble | Setting Time (seconds) Balsa | Setting Time (seconds) Lauan | Storage Stability (70° C. for 5 days) |
|---|---|---|---|---|---|---|
| Comparative Example No. | | | | | | |
| 5 | None | — | — | 40 | more than 300 | Good |
| 6 | Ethylene glycol | 1 | Yes | 40 | more than 300 | Good |

Table 2-continued

| Example/ Comparative Example No. | Polyethylene Glycol Type | n | Soluble | Setting Time (seconds) Balsa | Lauan | Storage Stability (70° C. for 5 days) |
|---|---|---|---|---|---|---|
| 7 | Diethylene glycol | 2 | Yes | 30 | 300 | Good |
| Example No. 9 | Triethylene glycol | 3 | Yes | 15 | 180 | Good |
| 10 | Tetraethylene glycol | 4 | Yes | 5 | 120 | Good |
| 11 | Polyethylene glycol 400 | 9 | Yes | 1 | 40 | Good |
| 12 | Polyethylene glycol 1500 | 35 | Yes | 1 | 30 | Good |
| 13 | Polyethylene glycol 6000 | 140 | Partly | 1 | 30 | Good |

It can be seen from the results in Table 2 that ethylene glycol and diethylene glycol whose degrees of polymerization are not more than 2 had a markedly low effect in shortening the setting time, but a marked effect of the addition of a polyethylene glycol was observed with triethylene glycol having a degree of polymerization of 3 or higher polyethylene glycols. The compression shear adhesion strengths of the adhesive compositions of Examples 9 to 13, measured under the same conditions as described in Example 1 on lauan wood, were 115 to 130 kg/cm² (the woody tissue broke).

EXAMPLE 14 AND COMPARATIVE EXAMPLE 8

To an α-cyanoacrylate-type adhesive comprising an isobutyl α-cyanoacrylate monomer, 40 ppm of sulfur dioxide and 200 ppm of hydroquinone monomethyl ether was added 0.2% of polyethylene oxide (Alcox E-45, a product of Meisei Chemical Co., Ltd.).

The setting time of the adhesive composition was measured in an atmosphere maintained at 23° C. and RH 55% on various adherends as indicated in Table 3 below.

As Comparative Example 8, the setting time of an α-cyanoacrylate adhesive composition having the composition described above but not containing the polyethylene oxide was also measured under the same conditions.

The results obtained are shown in Table 3 below.

The tensile adhesion strengths of the compositions of these examples on rigid vinyl chloride resin as an adherend were measured. The tensile adhesion strength was 370 kg/cm² in Example 14, and 355 kg/cm² in Comparative Example 8, showing hardly any significant difference therebetween.

The storage stability of each of the adhesive compositions of Example 14 and Comparative Example 8 was tested at 70°±2° C. for 5 days. Both of the adhesive compositions were found to have good storage stability.

Table 3

| Adherend | Setting Time (seconds) Example 14 | Comparative Example 8 |
|---|---|---|
| Balsa | 2 | 30 |
| Lauan | 30 | more than 300 |
| Lauan Veneer | 30 | more than 300 |
| Japan cedar | 10 | more than 300 |
| Spruce | 20 | more than 300 |
| Cherry | 15 | 180 |
| Rosewood | 5 | 15 |
| Alumina ceramic | 60 | more than 300 |
| Rigid polyvinyl chloride | 3 | 5 |
| Natural rubber | 2 | 3 |
| Iron | 15 | 45 |
| Aluminum | 5 | 90 |
| Corrugated cardboard | 5 | more than 300 |

While the invention has been described in detail and with reference to specific embodiments thereof, it will be apparent to one skilled in the art that various changes and modifications can be made therein without departing from the spirit and scope thereof.

What is claimed is:

1. An adhesive composition comprising an α-cyanoacrylate and about 0.0001% by weight to about 20% by weight, based on the weight of the adhesive composition, of at least one compound selected from the group consisting of
   (1) polyethylene glycols having a degree of polymerization of at least 3, and
   (2) non-ionic surface active agents having a poly(ethyleneoxy) moiety therein with the poly(ethyleneoxy) moiety having a degree of polymerization of at least 3.

2. The adhesive composition of claim 1, wherein said polyethylene glycols have a structure of the formula (II)

$$HO\text{-}(CH_2CH_2O)_n\text{H} \qquad (II)$$

wherein n represents the degree of polymerization and is at least 3.

3. The adhesive composition of claim 1, wherein said non-ionic surface active agents are selected from the group consisting of polyethylene glycol alkyl ether non-ionic surface active agents, polyethylene glycol alkyl phenyl ether non-ionic surface active agents, polyethylene glycol fatty acid ester non-ionic surface active agents, polyethylene glycol-polypropylene glycol ether non-ionic surface active agents, polyethylene glycol sorbitan fatty acid ester non-ionic surface active agents, ethylene oxide adducts of active hydrogen containing compounds and polyethylene glycol alkyl amine non-ionic surface active agents.

4. The adhesive composition of claim 1, wherein said α-cyanoacrylate is represented by the general formula (I)

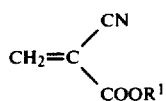

wherein R[1] represents a straight chain or branched chain alkyl group which may be substituted with a halogen atom or an alkoxy group, a straight or branched chain alkenyl group, a straight or branched chain alkynyl group, a cycloalkyl group, an aralkyl group or an aryl group.

5. The adhesive composition of claim 4, wherein R[1] is a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzoyl group, a phenyl group, a cresyl group, a 2-chloroethyl group, a 3-chloropropyl group, a 2-chlorobutyl group, a trifluoroethyl group, a 2-methoxyethyl group, a 3-methoxybutyl group, or a 2-ethoxyethyl group.

6. The adhesive composition of claim 1, wherein said adhesive composition additionally contains at least one of an anionic polymerization inhibitor, a radical polymerization inhibitor, a thickener, a plasticizer, a heat stabilizer, a perfume, and a colorant.

7. The adhesive composition of claim 1, wherein said polyethylene glycols have a degree of polymerization of 3 to about 10,000.

8. The adhesive composition of claim 1, wherein said polyethylene glycols have a degree of polymerization of 3 to about 3,000.

9. The adhesive composition of claim 1, wherein the poly(ethyleneoxy) moiety of said nonionic surface active agents has a degree of polymerization of 3 to about 200.

10. The adhesive composition of claim 1, wherein the poly(ethyleneoxy) moiety of said nonionic surface active agents has a degree of polymerization of 3 to about 100.